United States Patent
Kim et al.

(10) Patent No.: US 11,175,201 B2
(45) Date of Patent: Nov. 16, 2021

(54) CONTROL DEVICE AND AUTOMATIC WATER SAMPLER INCLUDING SAME

(71) Applicant: GEOENERGY CORPORATION, Gyeonggi-do (KR)

(72) Inventors: Hong Sun Kim, Gyeonggi-do (KR); Cheol Soo Myung, Incheon (KR)

(73) Assignee: GEOENERGY CORPORATION, Gyeonggi-do (KR)

( * ) Notice: Subject to any disclaimer, the term of this patent is extended or adjusted under 35 U.S.C. 154(b) by 213 days.

(21) Appl. No.: 16/657,138

(22) Filed: Oct. 18, 2019

(65) Prior Publication Data

US 2020/0116599 A1 Apr. 16, 2020

Related U.S. Application Data

(63) Continuation of application No. PCT/KR2018/004427, filed on Apr. 17, 2018.

(51) Int. Cl.
*G01N 33/18* (2006.01)
*G01N 1/14* (2006.01)
*G01N 35/10* (2006.01)

(52) U.S. Cl.
CPC .............. *G01N 1/14* (2013.01); *G01N 33/18* (2013.01); *G01N 35/1097* (2013.01)

(58) Field of Classification Search
CPC ...... G01N 1/14; G01N 33/18; G01N 35/1097; G01N 1/00; G01N 1/02; G01N 1/10; G01N 1/12

(Continued)

(56) References Cited

U.S. PATENT DOCUMENTS 3,489,012 A  1/1970  Niskin
3,537,316 A * 11/1970  Stewart .................. G01K 13/12
                                                      73/170.33

(Continued)

FOREIGN PATENT DOCUMENTS

CN   204422257 U   6/2015
JP     0388142     9/1991

(Continued)

OTHER PUBLICATIONS

EP18787807.9, "European Search Report", dated Dec. 21, 2020, 13 pages.

(Continued)

*Primary Examiner* — Robert R Raevis
(74) *Attorney, Agent, or Firm* — Kilpatrick Townsend & Stockton LLP

(57) ABSTRACT

An automatic water sampler is disclosed. The automatic water sampler of the present invention comprises: a driving unit operated according to the pressure measured by a pressure sensor; a driving magnet approaching a driven magnet according to the operation of the driving unit; and a first wire unlocked by a control rod according to the movement of the driven magnet. The present invention can provide an automatic water sampler, which improves inaccuracy due to conventional interference of an ocean current, flow velocity, and the like, and manual water sampling by depth by automatically sampling water at the correct depth recognized through a pressure sensor, thereby enabling reliability and accuracy of a sample to be ensured and sampling expenses to be remarkably reduced.

17 Claims, 5 Drawing Sheets

(58) Field of Classification Search
USPC ...... 73/864.34, 864.51, 864.63, 714; 116/70, 116/109, 112, 200, 204, 220, 227, 266, 116/267
See application file for complete search history.

(56) References Cited

U.S. PATENT DOCUMENTS

| | | | |
|---|---|---|---|
| 3,974,795 A | 8/1976 | Crisp | |
| 4,347,751 A | 9/1982 | Niskin et al. | |
| 4,846,004 A * | 7/1989 | Richards | G01N 1/12 73/864.63 |
| 4,852,413 A * | 8/1989 | Niskin | G01N 1/12 73/864.67 |
| 5,341,693 A * | 8/1994 | Banu | G01N 1/12 73/864.63 |
| 8,994,527 B2 * | 3/2015 | Verhulst | E21B 49/025 340/539.22 |
| 2018/0104436 A1 * | 4/2018 | Leonard | A61M 16/0096 |

FOREIGN PATENT DOCUMENTS

| | | |
|---|---|---|
| JP | 2006133206 A | 5/2006 |
| JP | 3181598 B2 | 1/2013 |
| KR | 20010026506 A | 4/2001 |
| KR | 200261997 | 2/2002 |
| KR | 100566541 B1 | 3/2006 |
| KR | 20090070182 A | 7/2009 |
| KR | 20090124278 A | 12/2009 |

OTHER PUBLICATIONS

JP2020-507969, "Office Action", dated Oct. 23, 2020, 6 pages.
PCT/KR2018/004427, "International Search Report and Written Opinion", dated Jul. 6, 2018, 9 pages.

* cited by examiner

CONTROL DEVICE AND AUTOMATIC WATER SAMPLER INCLUDING SAME

CROSS-REFERENCES TO RELATED APPLICATIONS

This application claims priority to and is a continuation of International Patent Application No. PCT/KR2018/004427, filed Apr. 17, 2018; which claims priority from Korean Patent Application No. KR 10-2017-0049966, filed Apr. 18, 2017, the entire contents of which are hereby incorporated by reference in their entirety for all purposes.

TECHNICAL FIELD

The present disclosure relates to a control device and an automatic water sampler including the same and, more particularly, to an automatic water sampler wherein the same is immersed in water to sample seawater or fresh water, a control rod moves such that an opening/closing cap seals the body thereof, and the same is particularly configured to sample water at a desired water level.

BACKGROUND OF THE INVENTION

Water samplers are equipment for sampling seawater or fresh water and are indispensable to analyzing water quality or sampling microorganisms or small plankton.

Existing water samplers are normally configured such that the same are connected to a wire and a rope, lowered underwater to a predetermined water level, and closed underwater by electric or mechanical impacts. Representative examples of water samplers include Nansen bottles and Niskin water samplers.

In the case of the Niskin water samplers, in particular, multiple water samplers can be installed to simultaneously sample water at different water levels, and there are no metallic components inside the water samplers. Accordingly, the Niskin water samplers are most widely used for water quality surveys.

FIG. 1A and FIG. 1B illustrate a Niskin water sampler. In FIG. 1A, parts of connection between the water sampler and a rope for lowering the same at a water level are marked by dotted circles. In FIG. 1B, a messenger portion for activating the water sampler is marked by a dotted circle.

However, there are shortcomings in that the bolt-type parts of connection between the rope and the water sampler pose a danger of getting loose when used. In addition, if the portion to be closed by the messenger is placed in an area with fast tidal currents as illustrated in FIG. 1B, the interval from the rope may increase, failing to sample water in many cases. Moreover, the handle portion and the rope-connecting part, which are connected to the body without using metallic materials, are weak and thus are easily fractured by minor impacts.

In addition, in order to sample and analyze specimens at respective water levels, sampling specimens at the exact water levels is crucial for precise analysis. In order to sample water at the desired water level by an existing water sampler, the exact water level at which the water sampler is positioned needs to be recognized, but sea currents and the like make it difficult to recognize the exact water level at which the water sampler is positioned.

In some cases, an existing water sampler is combined with a CTD in order to measure the water level, temperature, and the like which are necessary for precise measurements. However, this approach has a problem in that, in addition to increased costs, the water sampler needs to operated manually in each case.

Therefore, there is a need for development of a water level-recognizing water-sampler control device which is inexpensive and can be used while being attached to an existing water sampler, and a water sampler employing the same.

SUMMARY OF THE INVENTION

As one aspect of the present disclosure, an automatic water sample for sampling seawater or fresh water is provided, which comprises: a body immersed in water when sampling seawater or fresh water, the body having an inflow port and a sampling space provided therein; an opening/closing cap configured to open/close the inflow port; a control rod coupled to one side of the body to be able to make reciprocating movements; a first wire having one end connected to the opening/closing cap and the other end engaging with one side of the control rod, the opening/closing cap closing the inflow port when the first wire disengages from the control rod; and a control device coupled to one side of the body, the control device being coupled with the control rod by a second wire, wherein the control device is configured to operate according to a pressure measured by the control device to drive the control rod through the second wire to disengage the first wire from the control rod.

As another aspect of the present disclosure, a control device for the automatic water sampler is provided, which comprises: a first housing having a containing space formed therein; a driving magnet provided in the containing space; a driving unit provided in the containing space so as to move the driving magnet; a sensor cap screw-coupled to the first housing so as to seal the containing space, a through-hole being formed at the center of the sensor cap; a pressure sensor screw-coupled to the through-hole and positioned in the containing space so as to measure a water level; and a following magnet provided outside the first housing such that an attractive force or a repulsive force acts between the driving magnet and the following magnet, wherein the driving unit is configured to operate according to a pressure measured by the pressure sensor, and the driving magnet is configured to approach the following magnet in response to the operation of the driving unit.

DETAILED DESCRIPTION OF THE INVENTION

Technical Problem

Figure 1A:
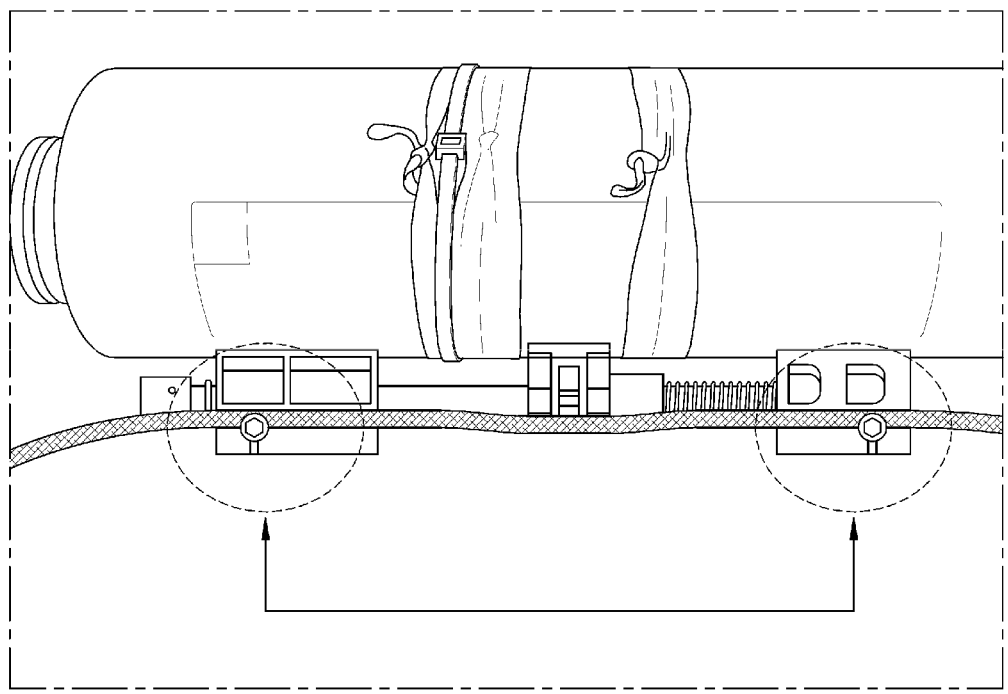
FIG. 1A and FIG. 1B are diagrams illustrating a conventional Niskin water sampler.
Figure 1B:
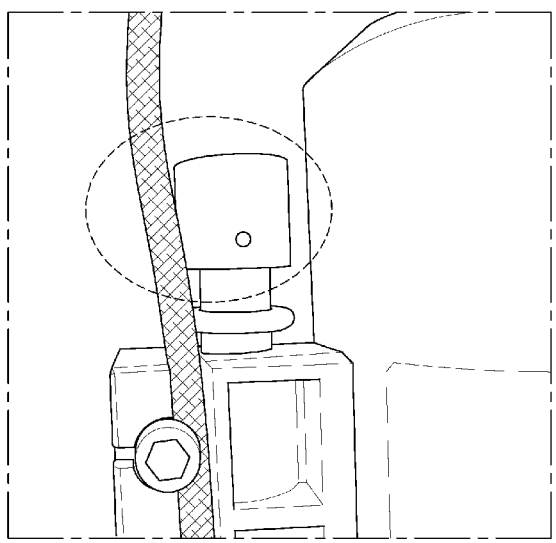

An aspect of the present disclosure is to provide a water sampler wherein water can be sampled at the exact water level necessary for water sampling, and control for water sampling can be accurately conducted even without moving a separate messenger by a rope.

Technical Solution

In accordance with an aspect of the present disclosure, there is provided an automatic water sampler including: a body immersed in water so as to sample seawater or fresh water, the body having an inflow port and a sampling space provided therein; an opening/closing cap configured to open/close the inflow port; a control rod coupled to one side of the body to be able to make reciprocating movements; a first wire having one end connected to the opening/closing cap and the other end engaging with one side of the control rod, the opening/closing cap closing the inflow port when the first wire disengages from the control rod; a first housing coupled to the body and having a containing space formed therein; a driving magnet provided in the containing space; a driving unit provided in the containing space so as to move the driving magnet; a pressure sensor coupled to the body or the first housing so as to measure a water level; and a following magnet provided outside the first housing such that an attractive force or a repulsive force acts between the driving magnet and the following magnet, wherein the driving unit is configured to operate according to a pressure measured by the pressure sensor, the driving magnet is configured to approach the following magnet in response to the operation of the driving unit, and the first wire is configured to disengage from the control rod in response to the movement of the following magnet.

The automatic water sampler according to the present disclosure may include: a fixing bracket fixed/coupled to the body so as to support the control rod which penetrates and is coupled to the fixing bracket; a first elastic body configured to elastically support the control rod in such a direction that the first wire disengages from the control rod; and a second wire having one end coupled to the following magnet and the other end coupled to the fixing bracket and the control rod while the first elastic body remains compressed by the control rod, wherein when the second wire and the control rod are uncoupled from each other in response to a movement of the following magnet, the control rod is moved by the first elastic body.

In connection with the automatic water sampler according to the present disclosure, the fixing bracket may have a bracket hole formed therein; the control rod may have a control hole formed therein; and, while the first elastic body remains compressed by the control rod, an end of the second wire may be successively inserted into the bracket hole and the control hole such that the second wire is coupled to the fixing bracket and the control rod.

The automatic water sampler according to the present disclosure may include: a second housing configured to contain the following magnet to be able to move; and a second elastic body provided inside the second housing so as to elastically support the following magnet in such a direction that the following magnet moves away from the driving magnet, wherein an attractive force acting between the driving magnet and the following magnet when the driving magnet approaches the following magnet to a maximum extent may be larger than an elastic force from the second elastic body.

The automatic water sampler according to the present disclosure may include: a third elastic body provided inside the second housing and positioned opposite to the second elastic body with reference to the following magnet so as to elastically support the following magnet in such a direction that the following magnet moves toward the driving magnet.

In connection with the automatic water sampler according to the present disclosure, the driving unit may include: a driving battery configured supply power to the pressure sensor; a driving motor configured to operate by power supplied through the driving battery; a control substrate configured to operate the driving motor according to the pressure measured by the pressure sensor; a driving gear coupled to a driving shaft of the driving motor; and a rack gear configured to mesh with the driving gear and to move linearly, the driving magnet being fixed/coupled to an end of the rack gear.

The automatic water sampler according to the present disclosure may include: a sensor cap screw-coupled to the first housing so as to seal the containing space, a through-hole being formed at the center of the sensor cap such that the pressure sensor is screw-coupled thereto; an O-ring interposed between the first housing and the sensor cap; and an inner fixing frame fixed inside the first housing so as to support the pressure sensor, the driving battery, the control substrate, and the driving motor to be aligned continuously, and to support the rack gear so as to move linearly without a clearance.

In accordance with another aspect of the present disclosure, there is provided a control device including: a first housing having a containing space formed therein; a driving magnet provided in the containing space; a driving unit provided in the containing space so as to move the driving magnet; a sensor cap screw-coupled to the first housing so as to seal the containing space, a through-hole being formed at the center of the sensor cap; a pressure sensor screw-coupled to the through-hole and positioned in the containing space so as to measure a water level; and a following magnet provided outside the first housing such that an attractive force or a repulsive force acts between the driving magnet and the following magnet, wherein the driving unit is configured to operate according to a pressure measured by the pressure sensor, and the driving magnet is configured to approach the following magnet in response to the operation of the driving unit.

Advantageous Effects

According to the present disclosure, it is possible to provide an automatic water sampler wherein water is automatically sampled at an accurate water level recognized by a pressure sensor such that, by removing the existing problems of interference by sea currents or flow velocities and inaccuracy resulting from manual water sampling at each water level, reliability and accuracy of specimens can be secured, and the sampling cost can be reduced substantially.

BRIEF DESCRIPTION OF MAJOR PARTS OF THE DRAWINGS

1: automatic water sampler
100: control device
110: first housing
120: driving magnet
130: driving unit
131: driving battery
132: driving motor
133: control substrate
134: driving gear
135: rack gear
140: sensor cap 141: through-hole
142: O-ring
150: pressure sensor
160: following magnet
170: second housing
171: second elastic body
172: third elastic body
180: inner fixing frame
181: front frame
182: rear frame
183: center frame
184: connecting rod
200: body
210: inlet port
220: sampling space
300: opening/closing cap
400: control rod
410: engaging ring
420: control hole
500: first wire
600: fixing bracket
610: bracket hole
700: first elastic body
800: second wire

MODE FOR CARRYING OUT THE INVENTION

Hereinafter, exemplary embodiments of the present disclosure will be described in detail with reference to the accompanying drawings. In the description of the present disclosure, the description of the well-known function or structure will be omitted in order to clear the subject matter of the present disclosure.

Figure 2:
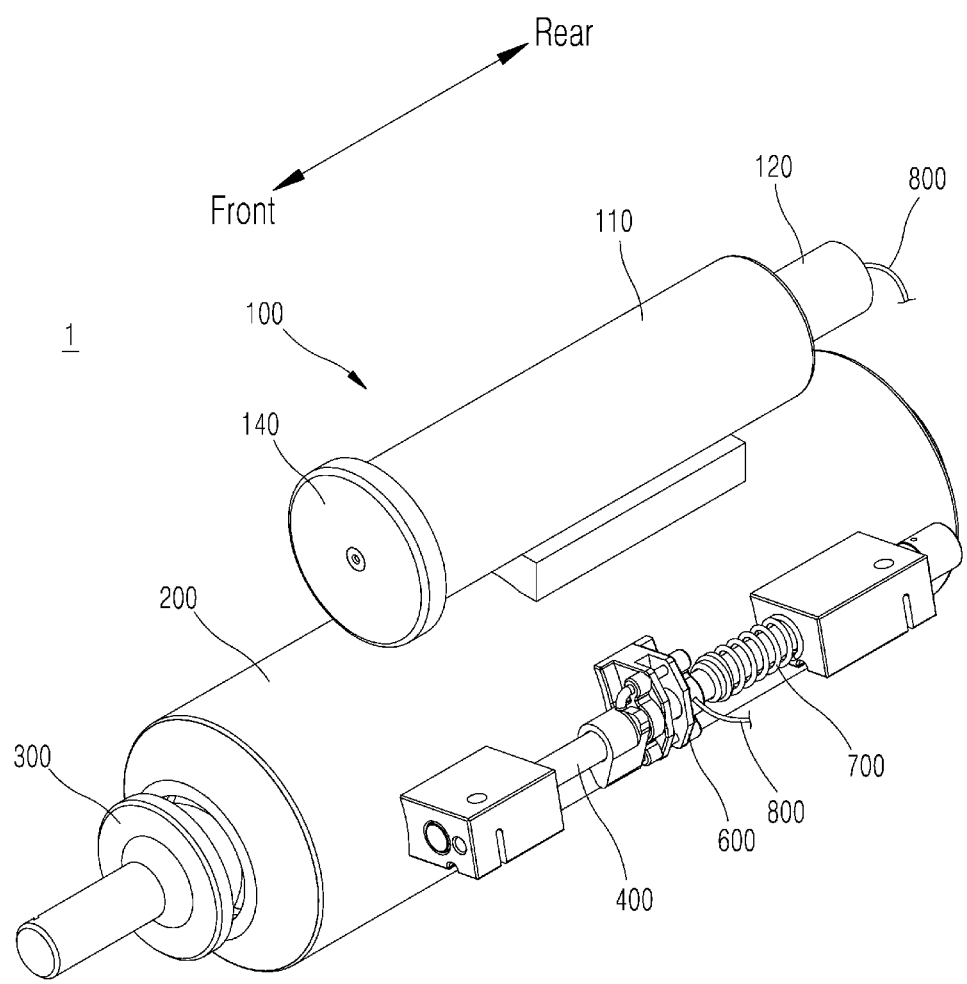
FIG. 2 is a perspective view of an automatic water sampler according to the present disclosure.
Figure 3:
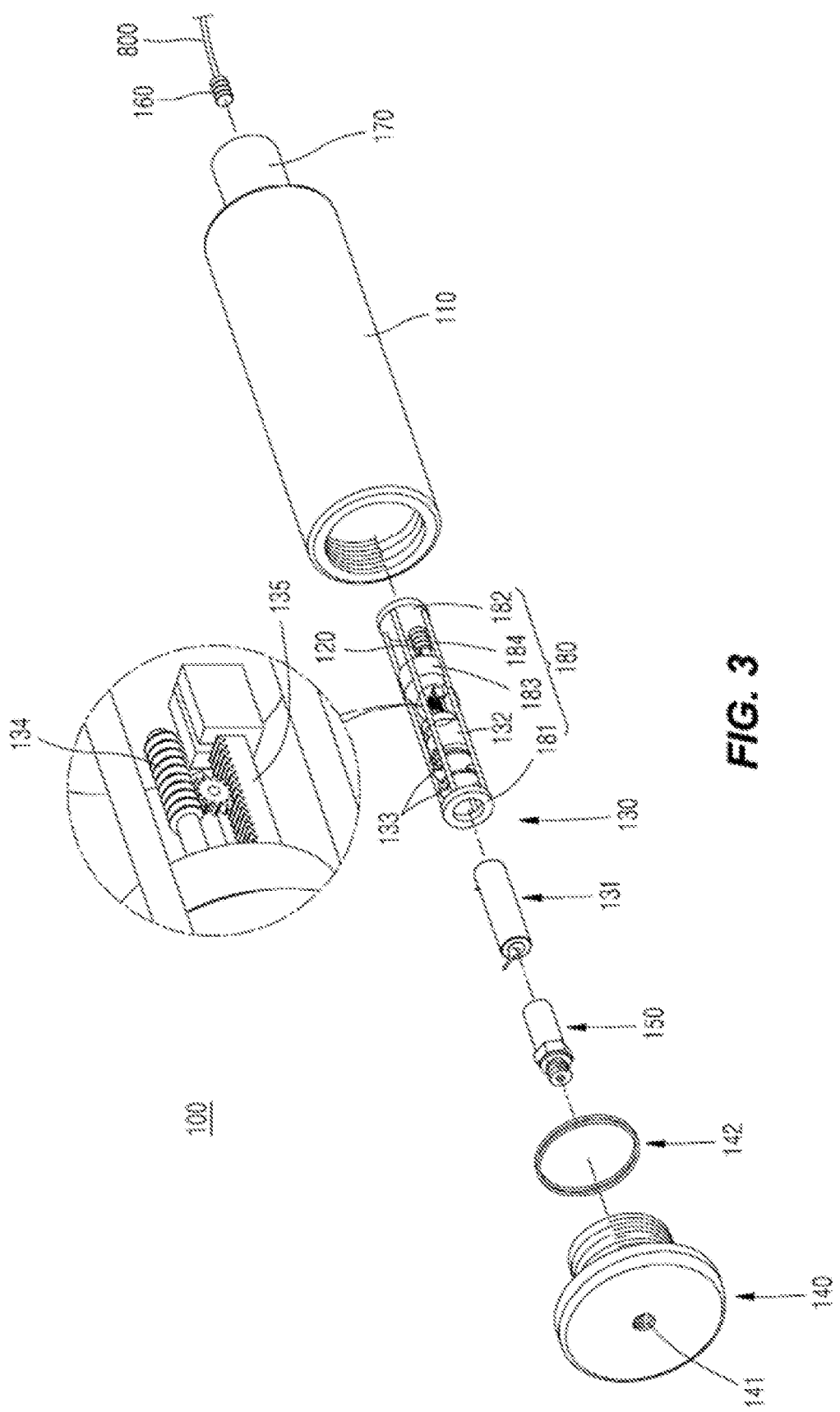
FIG. 3 is an exploded perspective view of the control device portion illustrated in FIG. 2.
Figure 4:
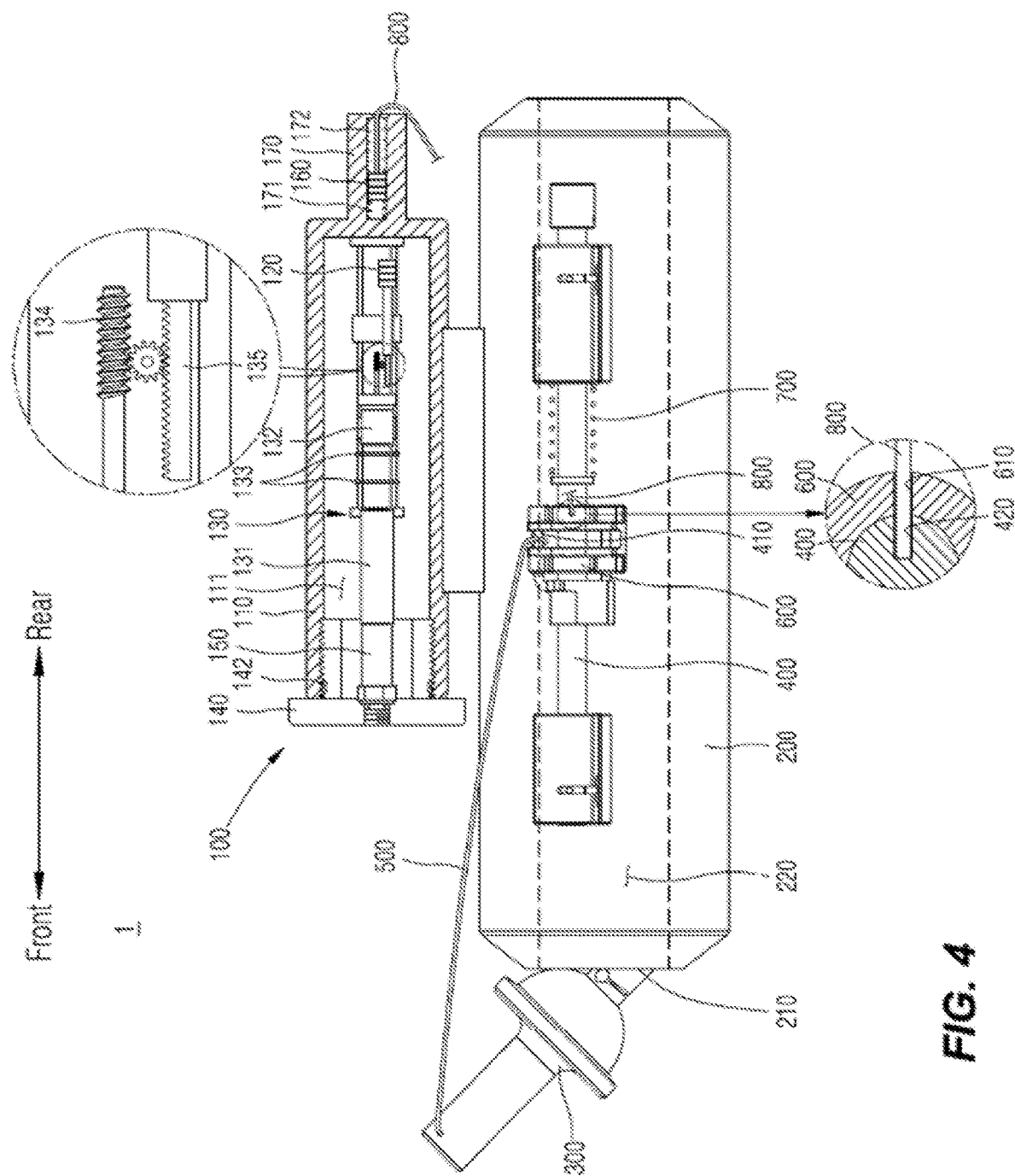
FIG. 4 and FIG. 5 are sectional views illustrating the operating state of the automatic water sampler illustrated in FIG. 2.
Figure 5:
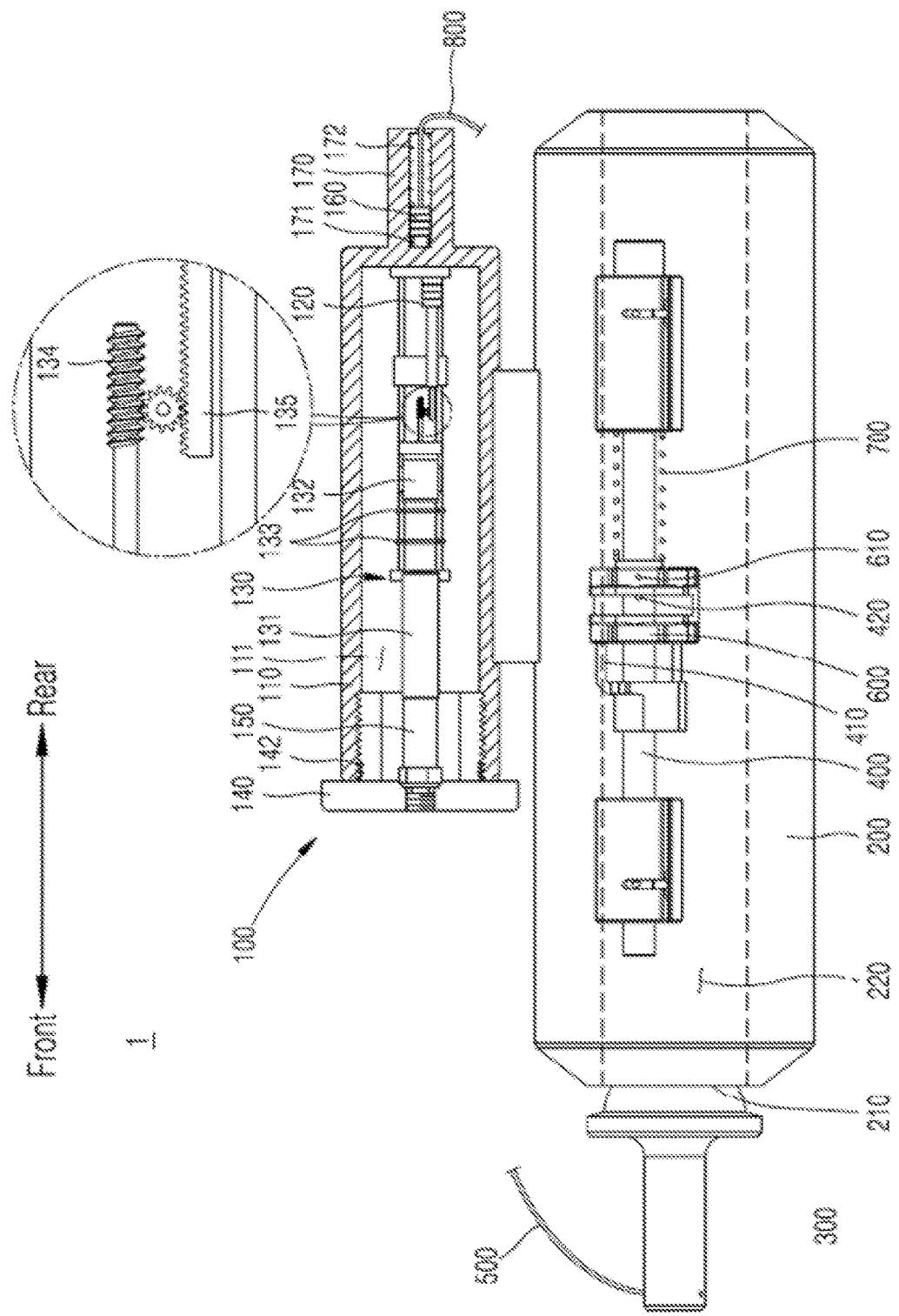

FIG. 2 is a perspective view of an automatic water sampler 1 according to the present disclosure; FIG. 3 is an exploded perspective view of the control device portion 100 illustrated in FIG. 2; and FIG. 4 and FIG. 5 are sectional views illustrating the operating state of the automatic water sampler 1 illustrated in FIG. 2.

The indication of "front" and "rear" sides in FIG. 2 is only for convenience of describing the control device 100 and the water sampler according to the present disclosure, and the "front" may be directed to the seabed or the sea surface during actual use of the control device 100 and the water sampler according to the present disclosure.

The control device 100 according to the present disclosure is a device used while being coupled to an automatic water sampler 1 so as to generate signals necessary for operations of the automatic water sampler 1 and operations thereof.

The automatic water sampler 1 including the control device 100 according to the present disclosure (hereinafter, simply referred to as "automatic water sampler 1") is a device immersed in water so as to sample seawater or fresh water, and includes a body 200, an opening/closing cap 300, a control rod 400, a first wire 500, and a control device 100. The control device 100 includes a first housing 110, a driving magnet 120, a driving unit 130, a pressure sensor 150, and a following magnet 160.

In addition, the automatic water sampler 1 may include a fixing bracket 600, a first elastic body 700, and a second wire 800. The control device 100 may include a second housing 170, a second elastic body 171, a sensor cap 140, an O-ring 142, and an inner fixing frame 180.

In addition, the control device 100 may further include a third elastic body 172.

The body 200 has an overall cylindrical shape and has an inflow portion 210 and a sampling space 220 provided therein. The inflow port 210 refers to a port through which seawater or fresh water to be sampled is introduced. The sampling space 220 refers to a space in which the introduced sample is stored.

It is not entirely impossible to form the inflow port 210 through only one side (front or rear side) of the body 200, but the inflow port 210 is preferably formed on both sides (front and rear sides) of the body 200.

The opening/closing cap 300 is configured to open/close the inflow port 210 of the body 200 such that the sampling space 220 of the body 200 communicates with the outside or is isolated therefrom. Although only one opening/closing cap 300 is illustrated in FIG. 2, FIG. 4 and FIG. 5, it would be obvious that, when the body 200 has inflow ports 210 formed through both sides (front and rear sides) thereof, two opening/closing caps 300 are accordingly provided and coupled to both sides (front and rear sides) of the body 200, respectively. This corresponds to a normal configuration of a water sampler, and detailed description thereof will be omitted herein.

When the automatic water sampler 1 according to the present disclosure is introduced underwater to sample water, the opening/closing cap 300 is coupled to the body 200 while the inflow port 210 of the body 200 remains open, and the opening/closing cap 300 seals the inflow port 210 at a point requiring water sampling.

The opening/closing cap 300 is configured to make a hinge rotation and to thereby open/close the inflow port 210 of the body 200. To this end, a separate hinge device may be provided (hinge device coupled between the opening/closing cap 300 and the body 200). Alternatively, no separate hinge device may be necessary. When no separate hinge device is provided, the opening/closing cap 300 may be pulled toward the sampling space 220 of the body 200 by a separate elastic band (rubber band), and the opening/closing cap 300 may thereby remain forced against the body 200.

The control rod 400 is coupled to one side of the body 200 to be able to make reciprocating movements, and a fixing bracket 600 is provided such that the control rod 400 is coupled.

The fixing bracket 600 is fixed/coupled to one side of the outer peripheral surface of the body 200. The control rod 400 is coupled to the fixing bracket 600 so as to penetrate the fixing bracket 600 in the forward/backward direction.

The control rod 400 may have an overall shape of a rod elongated along the forward/backward direction. An engaging ring 410 is formed on one side of the control rod 400. The engaging ring 410 makes reciprocating movements in the forward/backward direction together with the control rod 400, and the first wire 500 (described later) engages with the engaging ring 410.

The engaging 410 is also configured to penetrate the fixing bracket 600. When the engaging ring 410 moves backward and penetrates the fixing bracket 600, the first wire 500 engages with the engaging ring 410 (see FIG. 4; in this case, an end of the first wire 500 is restrained by the engaging ring 410 and the fixing bracket 600 and thus is prevented from detaching). When the engaging ring 410 moves relatively forward, the first wire 500 disengages from the engaging ring 410.

The first elastic body 700 is configured to elastically support the control rod 400 in such a direction that the first wire 500 disengages from the control rod 400 (engaging ring 410). With reference to FIG. 4, the first elastic body 700 elastically supports the control rod 400 such that the control rod 400 is pressurized forward.

The first elastic body 700 may include a conventional coil spring, and may be coupled to the control rod 400 while surrounding a part of the outer peripheral surface of the control rod 400.

The first wire 500 is configured in a long rope type. One side of the first wire 500 is connected and coupled to the opening/closing cap 300, and the other side thereof engages with the control rod 400, particularly the engaging ring 410, in a ring shape.

When both ends of the first wire 500 are connected to the opening/closing cap 300 and the engaging ring 410, respectively, the first wire 500 remains tightly tensioned. In this state, the opening/closing cap 300 keeps the inflow port 210 open (see FIG. 4).

If the control rod 400 moves (moves forward) in this state, the engaging ring 410 moves together, and the first wire 500 disengages from the engaging ring 410. In addition, the opening/closing cap 300 seals the inflow port 210 (see FIG. 5).

The control device 100 is fixed/coupled to one side of the outer peripheral surface of the body 200 so as to control an operation such that the first wire 500 disengages from the control rod 400 (the opening/closing cap 300 closes the inflow port 210).

The first housing 110 constituting the control device 100 constitutes the overall contour of the control device 100. The first housing 110 may be directly coupled to the outer peripheral surface of the body 200 or fixed/coupled to the body 200 via a separate constituent element.

The first housing 110 has an overall shape of a tube having a containing space 111 provided therein, and is elongated along the forward/backward direction. The first housing 110 may have the shape of a circular tube or a polygonal tube (including a quadrangular tube).

The first housing 110 is preferably made of a material having sufficient rigidity such that the shape thereof can be maintained against strong water pressure (when underwater) or external force applied thereto. In addition, the first housing 110 is preferably made of a material that has no or minimized influence on the magnetic force acting between the driving magnet 120 and the following magnet 160. Accordingly, the first housing 110 may be made of a non-magnetic material or may include the same. More specifically, the first housing 110 may be made of carbon fiber-reinforced plastic or engineering plastic, or may include the same.

The first housing 110 of the automatic water sampler 1 according to a preferred embodiment of the present disclosure may be shaped such that one side (front side) thereof is open, and the other side (rear side) thereof is sealed.

A sensor cap 140 may be coupled to the first housing 110. The sensor 140 may be coupled, particularly screw-coupled, to the opening (front side) of the first housing 110.

At least one O-ring 142 may be interposed between the first housing 110 and the sensor cap 140 such that, when the sensor cap 140 is coupled, sufficient airtightness is maintained.

The sensor cap 140 has a through-hole 141 formed through the center thereof in the forward/backward direction, and a pressure sensor 150 is screw-coupled to the through-hole 141.

The pressure sensor 150 according to the present disclosure may be a normal pressure sensor for measuring water pressure. A specific embodiment of the present disclosure employs a product PA-21SC available from Keller Inc.

As such, the control device 100 and the automatic water sampler 1 according to the present disclosure adopts a pressure sensor 150 for measuring the water level such that the exact water level can be confirmed at the actual point at which the control device 100 and the automatic water sampler 1 are positioned, and the accurate water level can be recognized even if the rope to which the automatic water sampler 1 is tied is bent by sea currents and the like.

As the pressure sensor 150 is coupled to the through-hole 141, one-side section of the pressure sensor 150 is exposed underwater, and the most part of the pressure sensor 150 is positioned in the containing space 111 of the first housing 110.

The driving magnet 120 is provided inside the containing space 111 and is configured to be able to make reciprocating movements, particularly to be able to make reciprocating movements in the forward/backward direction.

The driving unit 130 is provided in the containing space 111 and is configured to move the driving magnet 120.

The driving unit 130 may include a driving battery 131, a driving motor 132, a control substrate 133, a driving gear 134, and a rack gear 135.

The driving battery 131 may be configured to supply power to the pressure sensor 150 and may include a lithium ion battery.

The driving motor 132 may include a conventional electric motor and may be configured to operate by power supplied from the driving battery 131. The driving motor 132 may have a driving shaft elongated along the forward/backward direction, and the driving shaft may have an end facing backward.

The control substrate 133 is positioned between the driving battery 131 and the driving motor 132, and is configured to operate the driving motor 132 according to the pressure measured by the pressure sensor 150. To this end, the control substrate 133 may have elements coupled thereto, such as a CPU, a storage device, and a signal converter.

The control substrate 133 may include at least two separate parts. The control substrate 133 may have an overall shape of a flat plate, and may have a predetermined groove formed on a corner end thereof. A wire may be plated in the groove and electrically connected to the pressure sensor 150, the driving battery 131, and the driving motor 132.

The driving gear 134 is coupled to an end of the driving shaft of the driving motor 132.

The rack gear 135 is configured to mesh with the driving gear 134 directly/indirectly and to move linearly, particularly to move linearly in the forward/backward direction. The driving magnet 120 is fixed/coupled to the rear end of the rack gear 135.

The inner fixing frame 180 is fixed inside the first housing 110 so as to support the pressure sensor 150, the driving battery 131, the control substrate 133, and the driving motor 132 such that they are aligned continuously, and to support the rack gear 135 so as to move linearly with no clearance. To this end, the inner fixing frame 180 may include a front frame 181, a rear frame 182, a center frame 183, and a connecting rod 184.

The front frame 181 and the rear frame 182 may be configured as flat plates or circular rings, and are positioned on the front and rear sides, respectively. The front frame 181 may have a concave groove formed thereon such that the rear end of the driving battery 131 is tightly seated thereon. Alternatively, the front frame 181 may have a through-hole formed at the center thereof in the forward/backward direction such that the driving battery 131 is tightly fitted thereto. The front frame 181 may have a wire or the like provided thereon to be electrically connected to the driving battery 131, the driving motor 132, and the control board 133.

The rear frame 182 is tightly coupled to the rear wall of the first housing 110. The first housing 110 may have a concave groove formed on the inner surface of the rear wall thereof such that the rear frame 182 is tightly seated thereon and thus is stably coupled to the first housing 110.

The center frame 183 is positioned between the front frame 181 and the rear frame 182, and has a hole formed therein such that the rack gear 135 penetrates the same. That is, the rack gear 135 is coupled to the center frame 183 so as to penetrate the center framer 183, and is configured to be able to move forward/backward while being coupled to the center frame 183.

In order to facilitate the movement (forward/backward movement) of the rack gear 135 with regard to the center frame 183, one of the center frame 183 and the rack gear 135 may have a rail formed thereon so as to have a constant section along the forward/backward direction, and the other thereof may have a sider (having a constant section along the forward/backward direction) formed thereon so as to move along the rail.

The connecting rod 184 may be configured as a rod elongated in the forward/backward direction, and multiple connecting rods 183 may be provided. Each connecting rod 184 connects the front frame 181, the center frame 183, and the rear frame 182 to one another.

The control substrate 133 and the driving motor 132 may be tightly coupled in the space defined by coupling of the front frame 181, the center frame 183, and the connecting rod 184. The driving magnet 120 is positioned in the space defined by coupling of the front frame 181, the center frame 183, and the connecting rod 184.

Such a configuration guarantees an efficient operation of the control device 100 while minimizing the volume of the control device 100, and secures durability of the control device 100 against strong water pressure and external impacts.

The following magnet 160 is provided on the outside of the first housing 110, and is configured such that an attractive force or a repulsive force acts between the same and the driving magnet 120.

In connection with the automatic water sampler 1 according to the present disclosure, one of the driving magnet 120 and the following magnet 160 may be made of a permanent magnet, and the other thereof may be made of a material that can exhibit an attractive force or a repulsive force with the permanent magnet. However, both the driving magnet 120 and the following magnet 160 are preferably made of permanent magnets such that a strong magnetic force is exerted stably.

The driving magnet 120 and the following magnet 160 are spaced apart from each other with the wall (rear wall) of the first housing 110 serving as a boundary. Particularly, if the driving magnet 120 is moved backward by operation of the driving unit 130 while a sufficient spacing distance exists between the driving magnet 120 and the following magnet 160 (sufficient to ignore the magnetic force acting between the driving magnet 120 and the following magnet 160), an attractive force or a repulsive force then acts and moves the following magnet 160 forward or backward.

The control device 100 and the automatic water sampler 1 including the same, according to the present disclosure, are configured such that a movement of the driving magnet 120 causes a movement of the following magnet 160 as describe above, and such a movement of the following magnet 160 is used as a signal or an operation for sealing the inflow port 210 of the body 200 by the opening/closing cap 300.

Although the automatic water sampler 1 according to the present disclosure described with reference to FIG. 2 to FIG. 5 is configured such that an attractive force acts between the driving magnet 120 and the following magnet 160, it would be obvious that, according to various modified embodiments, a case in which a repulsive force acting between the driving magnet 120 and the following magnet 160 may be used as a signal or an operation for the opening/closing cap 300 to seal the inflow port 210 of the body 200.

The following description will be made with reference to the case in which an attractive force acts between the driving magnet 120 and the following magnet 160.

The second housing 170 has an overall shape of a tube which has a space provided therein, and which is elongated in the forward/backward direction. The second housing 170 may have the shape of a circular tube or a polygonal tube (including a quadrangular tube).

The second housing 170 is fixed/coupled to the rear end of the first housing 110.

The following magnet 160 is configured to be able to move in the forward/backward direction inside the second housing 170. In order to prevent the following magnet 160 from moving in directions other than the forward/backward direction, the following magnet 160 preferably has an outer diameter equal or close to the inner diameter of the second housing 170.

The second housing 170 may have a second elastic body 171 provided therein, and may have a third elastic body 172 additionally provided therein.

The second elastic body 171 elastically supports the following magnet 160 away from the driving magnet 120. Specifically, the second elastic body 171 may be configured as a conventional coil spring positioned in front of the following magnet 160.

When the following magnet 160 and the second elastic body 171 are provided inside the second housing 170 (when no third elastic body 172 is provided), and when the driving magnet 120 and the following magnet 160 are sufficiently spaced apart from each other (to such an extent that the attractive force acting between the driving magnet 120 and the following magnet 160 is neglectable), the following magnet 160 is preferably positioned rearmost in the second housing 170.

Accordingly, if the attractive force with the driving magnet 120 moves the following magnet 160 forward, the following magnet 160 compresses the second elastic body 171, which then can accumulate elastic energy.

Furthermore, in connection with the control device 100 and the automatic water sampler 1 according to the present disclosure, the attractive force acting between the driving magnet 120 and the following magnet 160 when the driving magnet 120 approaches the following magnet 160 to the largest extent is larger than the elastic force from the second elastic body 171. The second elastic body 171 is compressed until a balance is reached between the attractive force acting between the driving magnet 120 and the following magnet 160 and the elastic force from the second elastic body 171.

The second elastic body 171 provided in the second housing 170 in the above-mentioned manner guarantees that a predetermined distance is maintained between the driving magnet 120 and the following magnet 160, and prevents an operational error caused by an unwanted movement of the following magnet 160 inside the second housing 170.

The third elastic body 172 is provided inside the second housing 170 and is positioned opposite to the second elastic body 171 with reference to the following magnet 160 so as to elastically support the following magnet 160 toward the driving magnet 120.

The third elastic body 172 may also be configured as a conventional coil spring.

When the driving magnet 120 and the following magnet 160 are sufficiently spaced apart from each other (to such an extent that the attractive force acting between the driving magnet 120 and the following magnet 160 is neglectable), the following magnet 160 remains in a predetermined position inside the second housing 170 by means of the second elastic body 171 and the third elastic body 172.

In addition, the third elastic body 172 helps the second wire 800 which connects the following magnet 160 and the control rod 400, as will be described later, such that the second wire 800 remains tightly tensioned, thereby preventing an operational error caused by unwanted loosening of the second wire 800.

The second wire 800 is configured as a long rope or a long string, one side of which is coupled to the following magnet 160, and the other side of which is coupled to the fixing bracket 600 and the control rod 400.

The second wire 800 may be made of a material that enables the same to bend flexibly as a whole, such as metal, synthetic resin, or fiber. Parts of the second wire 800 coupled to the fixing bracket 600 and the control rod 400 (parts inserted into the bracket hole 610 and the control hole 420 described later) may be made of a material harder than other parts.

In connection with the automatic water sampler 1 according to the present disclosure, when one end of the second wire 800 is coupled to the following magnet 160, and when the other end thereof is coupled to the fixing bracket 600 and the control rod 400, the second wire 800 remains tightly tensioned without loosening.

The second wire 800 is fixed/coupled to the following magnet 160 inseparably, but is separably coupled to the fixing bracket 600 and the control rod 400.

For coupling with the second wire 800, the fixing bracket 600 has a bracket hole 610 formed therein, and the control rod 400 has a control hole 420 formed therein (see FIG. 4).

Each of the bracket hole 610 and the control hole 420 is sized such that the second wire 800 can be inserted therein. The inner diameter of each of the bracket hole 610 and the control hole 420 may be equal to or slightly larger than the outer diameter of the end of the second wire 800.

Since the control rod 400 is configured to be able to make reciprocating movements forward/backward with reference to the fixing bracket 600 as described above, the bracket hole 610 and the control hole 420 may be positioned close to each other or spaced apart from each other, depending on the position of the control rod 400.

In connection with the automatic water sampler 1 according to an embodiment of the present disclosure, the bracket hole 610 and the control hole 420 may be positioned closest to each other when the control rod 400 has moved relatively backward and thus has compressed the first elastic body 700, and the bracket hole 610 and the control hole 420 may be particularly positioned on the same line in this case.

In this state, the end of the second wire 800 may be successively inserted into the bracket hole 610 and the control hole 420. If no separate external force acts while the end of the second wire 800 is inserted into the bracket hole 610 and the control hole 420, the elastic force from the first elastic body 700 tends to move the control rod 400 forward. In addition, the end of the second wire 800 keeps engaging with the bracket hole 610 and the control hole 420, and the control rod 400 is prevented from moving (moving forward) with regard to the fixing bracket 600.

If the driving magnet 120 moves backward and thus increases the attractive force between the driving magnet 120 and the following magnet 160, thereby moving the following magnet 160 (forward), the second wire 800 is pulled, thereby withdrawing the end part of the second wire 800 from the control hole 420 (or from the control hole 420 and the bracket hole 610). The control rod 400 is pressurized by the first elastic body 700 and is moved forward. The engaging ring 410 moves together, and the end of the first wire 500 is released from the engaging ring 410. In addition, the opening/closing cap 300 seals the inflow port 210.

As described above, the control device 100 and the automatic water sampler 1 according to the present disclosure make it possible to automatically sample water at an accurate water level recognized by the pressure sensor 150 such that, by removing the existing problems of interference by sea currents or flow velocities and inaccuracy resulting from manual water sampling at each water level, reliability and accuracy of specimens can be secured, and the sampling cost can be reduced substantially. In addition, a signal and an operation for sampling water can be accurately generated even without separately moving a messenger by a rope, and water can be sampled accurately at the desired point.

Although the specific embodiment of the present disclosure has been described above, it is apparent to those skilled in the art that the present disclosure is not limited to the embodiment disclosed herein and various modifications and changes can be made without departing from the spirit and scope of the present disclosure. Therefore, such modifications and changes should not be individually construed from the spirit or point of view of the present disclosure, and it should be understood that modified embodiments belong to the claims of the present disclosure.

INDUSTRIAL APPLICABILITY

According to the present disclosure, it is possible to provide an automatic water sampler wherein water is automatically sampled at an accurate water level recognized by a pressure sensor such that, by removing the existing problems of interference by sea currents or flow velocities and inaccuracy resulting from manual water sampling at each water level, reliability and accuracy of specimens can be secured, and the sampling cost can be reduced substantially. As such, the present disclosure can overcome the limits of existing technologies and is not only applicable in the relevant technical field, but also endows the devices to which the present disclosure is applied with sufficient marketing or business potentials. The present disclosure can also be implemented obviously on a realistic basis. Therefore, the present disclosure is industrially applicable.

What is claimed is:

1. An automatic water sampler comprising:
a body immersed in water when sampling seawater or fresh water, the body having an inflow port and a sampling space provided therein;
an opening/closing cap configured to open/close the inflow port;
a control rod coupled to one side of the body operable to make reciprocating movements;
a first wire having one end connected to the opening/closing cap and the other end engaging with one side of the control rod, the opening/closing cap closing the inflow port when the first wire disengages from the control rod; and a control device coupled to one side of the body, the control device being coupled with the control rod by a second wire, wherein the control device is configured to operate according to a pressure measured by the control device to drive the control rod through the second wire to disengage the first wire from the control rod.

2. The automatic water sampler of claim 1, wherein the control device comprises:
a first housing coupled to the body and having a containing space formed therein;
a driving magnet provided in the containing space;
a driving unit provided in the containing space so as to move the driving magnet;
a pressure sensor coupled to the body or the first housing so as to measure the pressure; and
a following magnet provided outside the first housing such that an attractive force or a repulsive force acts between the driving magnet and the following magnet, wherein
the driving unit is configured to operate according to the pressure measured by the pressure sensor, the driving magnet is configured to approach the following magnet in response to the operation of the driving unit, and the first wire is configured to disengage from the control rod in response to movement of the following magnet.

3. The automatic water sampler of claim 2, further comprising:
a fixing bracket coupled to the body so as to support the control rod that penetrates and is coupled to the fixing bracket; and
a first elastic body configured to elastically support the control rod in such a direction that the first wire disengages from the control rod;
wherein the second wire having one end coupled to the following magnet and the other end coupled to the fixing bracket and the control rod while the first elastic body remains compressed by the control rod, and
when the second wire and the control rod are uncoupled from each other in response to a movement of the following magnet, the control rod is moved by the first elastic body.

4. The automatic water sampler of claim 3, wherein the fixing bracket has a bracket hole formed therein, the control rod has a control hole formed therein, and, while the first elastic body remains compressed by the control rod, an end of the second wire is successively inserted into the bracket hole and the control hole such that the second wire is coupled to the fixing bracket and the control rod.

5. The automatic water sampler of claim 2, wherein the control device further comprises:
a second housing configured to contain the following magnet to be able to move; and
a second elastic body provided inside the second housing so as to elastically support the following magnet in such a direction that the following magnet moves away from the driving magnet, wherein
an attractive force acting between the driving magnet and the following magnet when the driving magnet approaches the following magnet to a maximum extent is larger than an elastic force from the second elastic body.

6. The automatic water sampler of claim 5, wherein the control device further comprises a third elastic body provided inside the second housing and positioned opposite to the second elastic body with reference to the following magnet so as to elastically support the following magnet in such a direction that the following magnet moves toward the driving magnet.

7. The automatic water sampler of claim 2, wherein the driving unit comprises:
a driving battery configured supply power to the pressure sensor;
a driving motor configured to operate by power supplied through the driving battery;
a control substrate configured to operate the driving motor according to the pressure measured by the pressure sensor;
a driving gear coupled to a driving shaft of the driving motor; and
a rack gear configured to mesh with the driving gear and to move linearly, the driving magnet being coupled to an end of the rack gear.

8. The automatic water sampler of claim 7, wherein the control device further comprises:
a sensor cap screw-coupled to the first housing so as to seal the containing space, a through-hole being formed at the center of the sensor cap such that the pressure sensor is screw-coupled thereto;
an O-ring interposed between the first housing and the sensor cap; and
an inner fixing frame fixed inside the first housing so as to support the pressure sensor, the driving battery, the control substrate, and the driving motor to be aligned continuously, and to support the rack gear so as to move linearly without a clearance.

9. The automatic water sampler of claim 2, wherein the first housing comprises a non-magnetic material.

10. The automatic water sampler of claim 9, wherein the non-magnetic material includes carbon fiber-reinforced plastic or engineering plastic.

11. A control device comprising:
a first housing having a containing space formed therein;
a driving magnet provided in the containing space;
a driving unit provided in the containing space so as to move the driving magnet;
a sensor cap screw-coupled to the first housing so as to seal the containing space, a through-hole being formed at the center of the sensor cap;
a pressure sensor screw-coupled to the through-hole and positioned in the containing space so as to measure a water level; and
a following magnet provided outside the first housing such that an attractive force or a repulsive force acts between the driving magnet and the following magnet,
wherein the driving unit is configured to operate according to a pressure measured by the pressure sensor, and the driving magnet is configured to approach the following magnet in response to the operation of the driving unit.

12. The control device of claim 11, further comprising:
a second housing configured to contain the following magnet operable to move; and
a second elastic body provided inside the second housing so as to elastically support the following magnet in such a direction that the following magnet moves away from the driving magnet,
wherein an attractive force acting between the driving magnet and the following magnet when the driving magnet approaches the following magnet to a maximum extent is larger than an elastic force from the second elastic body.

13. The control device of claim 12, further comprising a third elastic body provided inside the second housing and positioned opposite to the second elastic body with reference to the following magnet so as to elastically support the following magnet in such a direction that the following magnet moves toward the driving magnet.

14. The control device of claim 11, wherein the driving unit comprises:
- a driving battery configured supply power to the pressure sensor;
- a driving motor configured to operate by power supplied through the driving battery;
- a control substrate configured to operate the driving motor according to the pressure measured by the pressure sensor;
- a driving gear coupled to a driving shaft of the driving motor; and
- a rack gear configured to mesh with the driving gear and to move linearly, the driving magnet being coupled to an end of the rack gear.

15. The control device of claim 14, further comprising:
- an O-ring interposed between the first housing and the sensor cap; and
- an inner fixing frame fixed inside the first housing so as to support the pressure sensor, the driving battery, the control substrate, and the driving motor to be aligned continuously, and to support the rack gear so as to move linearly without a clearance.

16. The control device of claim 11, wherein the first housing comprises a non-magnetic material.

17. The control device of claim 16, wherein the non-magnetic material includes carbon fiber-reinforced plastic or engineering plastic.

* * * * *

UNITED STATES PATENT AND TRADEMARK OFFICE
CERTIFICATE OF CORRECTION

| | |
|---|---|
| PATENT NO. | : 11,175,201 B2 |
| APPLICATION NO. | : 16/657138 |
| DATED | : November 16, 2021 |
| INVENTOR(S) | : Hong Sun Kim and Cheol Soo Myung |

It is certified that error appears in the above-identified patent and that said Letters Patent is hereby corrected as shown below:

On the Title Page

"Foreign Application Priority Data" Item (30), please insert -- KR 10-2017-0049966 filed on April 18, 2017 --

Signed and Sealed this
Twenty-third Day of May, 2023

Katherine Kelly Vidal
*Director of the United States Patent and Trademark Office*